US008434488B2

(12) United States Patent
Li et al.

(10) Patent No.: US 8,434,488 B2
(45) Date of Patent: May 7, 2013

(54) ENDOTRACHEAL TUBE WITH DEDICATED EVACUATION PORT

(75) Inventors: Youzhi Li, Longmont, CO (US); Bo Chen, Louisville, CO (US)

(73) Assignee: Covidien LP, Mansfield, MA (US)

( * ) Notice: Subject to any disclaimer, the term of this patent is extended or adjusted under 35 U.S.C. 154(b) by 666 days.

(21) Appl. No.: 12/480,394

(22) Filed: Jun. 8, 2009

(65) Prior Publication Data
US 2010/0307508 A1  Dec. 9, 2010

(51) Int. Cl.
*A61M 16/04* (2006.01)
*A61M 16/00* (2006.01)

(52) U.S. Cl.
USPC .................................. 128/207.15; 128/207.16

(58) Field of Classification Search ............ 128/207.15, 128/200.26, 207.14, 207.16; 606/192, 194, 606/196; 604/101.01, 101.04
See application file for complete search history.

(56) References Cited

U.S. PATENT DOCUMENTS

| | | | |
|---|---|---|---|
| 3,810,474 A * | 5/1974 | Cross ........................ | 128/207.15 |
| 4,305,392 A | 12/1981 | Chester | |
| 5,067,497 A * | 11/1991 | Greear et al. ............. | 128/207.15 |
| 5,201,310 A * | 4/1993 | Turnbull .................... | 128/207.15 |
| 5,311,864 A * | 5/1994 | Huerta ...................... | 128/207.15 |
| 5,313,939 A | 5/1994 | Gonzalez | |
| 5,315,992 A | 5/1994 | Dalton | |
| 5,803,898 A * | 9/1998 | Bashour ...................... | 600/120 |
| 5,819,723 A * | 10/1998 | Joseph ....................... | 128/207.14 |
| 6,725,862 B2 | 4/2004 | Klinberg et al. | |
| 7,089,942 B1 * | 8/2006 | Grey ........................ | 128/207.14 |
| 7,191,782 B2 | 3/2007 | Madsen | |
| 7,503,328 B2 | 3/2009 | Kolobow et al. | |
| 7,581,541 B2 * | 9/2009 | Madsen et al. ........... | 128/207.14 |
| 7,654,264 B2 * | 2/2010 | Clayton .................... | 128/207.15 |
| 7,921,847 B2 * | 4/2011 | Totz ......................... | 128/207.15 |
| 2002/0157665 A1 | 10/2002 | Igarashi et al. | |
| 2003/0145860 A1 | 8/2003 | Johnson | |
| 2008/0035154 A1 | 2/2008 | Johnson | |
| 2008/0047562 A1 | 2/2008 | Colburn et al. | |
| 2008/0053454 A1 * | 3/2008 | Pasillas et al. ........... | 128/207.15 |
| 2008/0099025 A1 | 5/2008 | MacMillan | |

(Continued)

FOREIGN PATENT DOCUMENTS

| | | |
|---|---|---|
| CA | 2463538 A1 | 9/2002 |
| EP | 0 766 976 A2 | 4/1997 |

(Continued)

OTHER PUBLICATIONS

Bassi, Gianluigi Li et al.; "Following tracheal intubation, mucus flow is reversed in the semirecumbent position: Possible role in the pathogenesis of ventilator-associated pneumonia"; Crit Care Med 2007, vol. 36, No. 2, pp. 518-525.

(Continued)

*Primary Examiner* — Stephen Crow

(57) ABSTRACT

Various embodiments of a tracheal tube capable of suctioning accumulated mucus secretions from the airway of intubated patients are provided. Disclosed embodiments include a variety of endotracheal tubes with integral suction lumens terminating in ports optimally located at the distal end of the endotracheal tubes between a Murphy's Eye and a cuff. During intubation, the foregoing features, among others, of the tracheal tube may have the effect of preventing bacterial colonization of the respiratory airway and the subsequent development of ventilator associated pneumonia (VAP) in the lungs.

20 Claims, 5 Drawing Sheets

U.S. PATENT DOCUMENTS

| | | |
|---|---|---|
| 2009/0038620 A1 | 2/2009 | Efrati |
| 2009/0071484 A1 | 3/2009 | Black et al. |
| 2009/0125002 A1* | 5/2009 | Totz ............................. 604/528 |
| 2009/0229605 A1 | 9/2009 | Efrati et al. |
| 2009/0288665 A1* | 11/2009 | Coates .................... 128/207.14 |
| 2010/0006102 A1* | 1/2010 | Schnell et al. ........... 128/207.14 |
| 2010/0186749 A1* | 7/2010 | Macan et al. ............ 128/207.15 |
| 2010/0307508 A1* | 12/2010 | Li et al. .................... 128/207.15 |
| 2011/0265799 A1* | 11/2011 | Lisogurski ............... 128/207.15 |
| 2011/0265800 A1* | 11/2011 | Baska ...................... 128/207.15 |

FOREIGN PATENT DOCUMENTS

| | | |
|---|---|---|
| EP | 1 806 158 A1 | 11/2007 |
| WO | 2005009522 A1 | 2/2005 |
| WO | 2008027575 A1 | 3/2008 |

OTHER PUBLICATIONS

Bassi, Gianluigi Li et al.; "A 72-hour study to test the efficacy and safety of the 'Mucus Slurper' in mechanically ventilated sheep"; Crit Care Med 2007, vol. 35, No. 3, pp. 906-911.

Branson, Richard D.; "Secretion Managemetn in the Mechanically Ventilated Patient"; Respiratory Care; Oct. 2007, vol. 52, No. 10, pp. 1328-1347.

Kolobow, Theodor; "The Mucus Slurper: a novel tracheal tube that requires no tracheal tube suctioning. A preliminary report"; Intensive Care Med, (2006) 32:1414-1418.

International Search Report for application No. PCT/US2010/037005 mailed Aug. 5, 2010 (PCT/ISA/210) pp. 1-2.

* cited by examiner

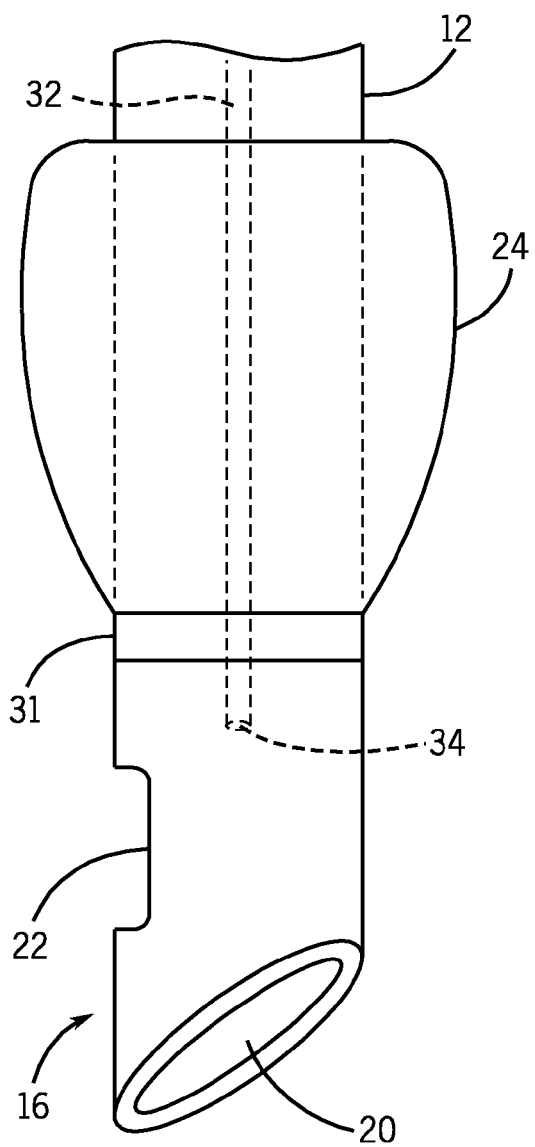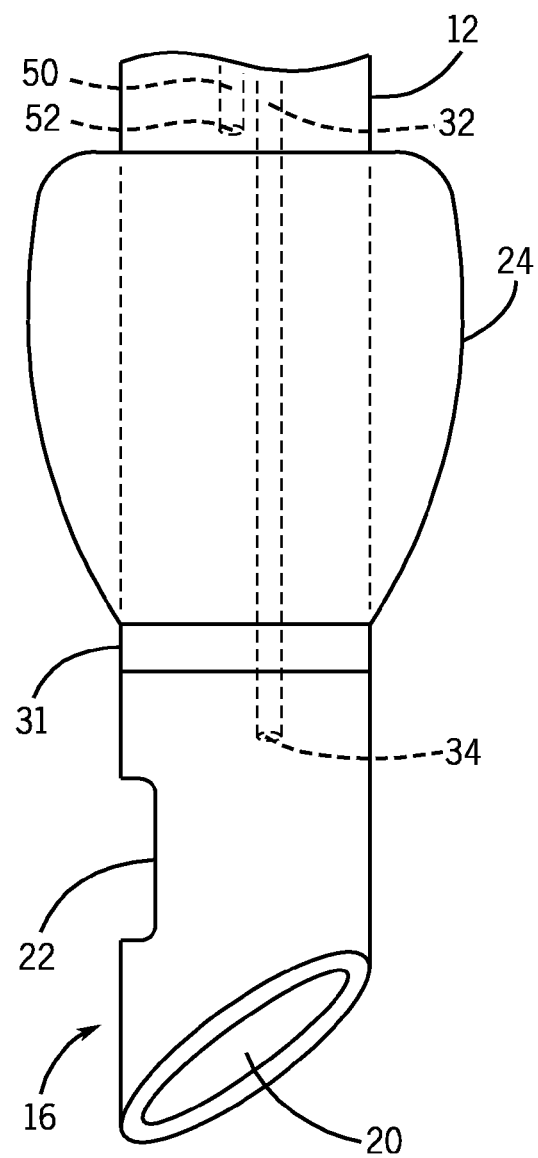

ENDOTRACHEAL TUBE WITH DEDICATED EVACUATION PORT

BACKGROUND

The present disclosure relates generally to medical devices and, more particularly, to airway devices, such as tracheal tubes.

This section is intended to introduce the reader to aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Endotracheal tubes are often placed in the airway of a patient in medical situations that necessitate protection of the airway from possible obstruction or occlusion. For instance, tracheal tubes may be used in emergency situations, such as when a patient experiences cardiac or respiratory arrest. Such intubations increase a patient's risk of developing ventilator-associated pneumonia (VAP) due to bacterial colonization of the lower respiratory airways. In healthy individuals, mucociliary clearance removes particles and microorganisms, which helps prevent respiratory infection. However, in critically ill patients, clearance mechanisms are compromised due to tracheal tube cuff inflation, and mucus accumulates at the distal end of the tracheal tube below the cuff. In many instances, such critically ill patients may remain intubated for extensive periods of time, during which mucus accumulated at the bottom of the cuff may drop to the proximal trachea and ultimately infect the lungs.

In many instances, it may be desirable to manage the accumulation of mucus secretions around the cuff via removal through external suctioning, administration of antibiotics, or a combination thereof. Some endotracheal tubes exclusively target mucus secretions accumulated in the area above the cuff. However, these systems fail to adequately address the accumulation of mucus secretions below the cuff. Additionally, traditional designs often include further drawbacks, such as requirements for the assembly and addition of supplementary parts that are not integral to the tracheal tube.

BRIEF DESCRIPTION OF THE DRAWINGS

Advantages of the present disclosure may become apparent upon reading the following detailed description and upon reference to the drawings in which:

FIG. 2 is an elevational view of the distal end of the exemplary endotracheal tube of FIG. 1 in accordance with aspects of the present disclosure;

FIG. 5 is an elevational view of the distal end of the exemplary endotracheal tube of FIG. 4 in accordance with aspects of the present disclosure;

DETAILED DESCRIPTION OF SPECIFIC EMBODIMENTS

Figure 1:
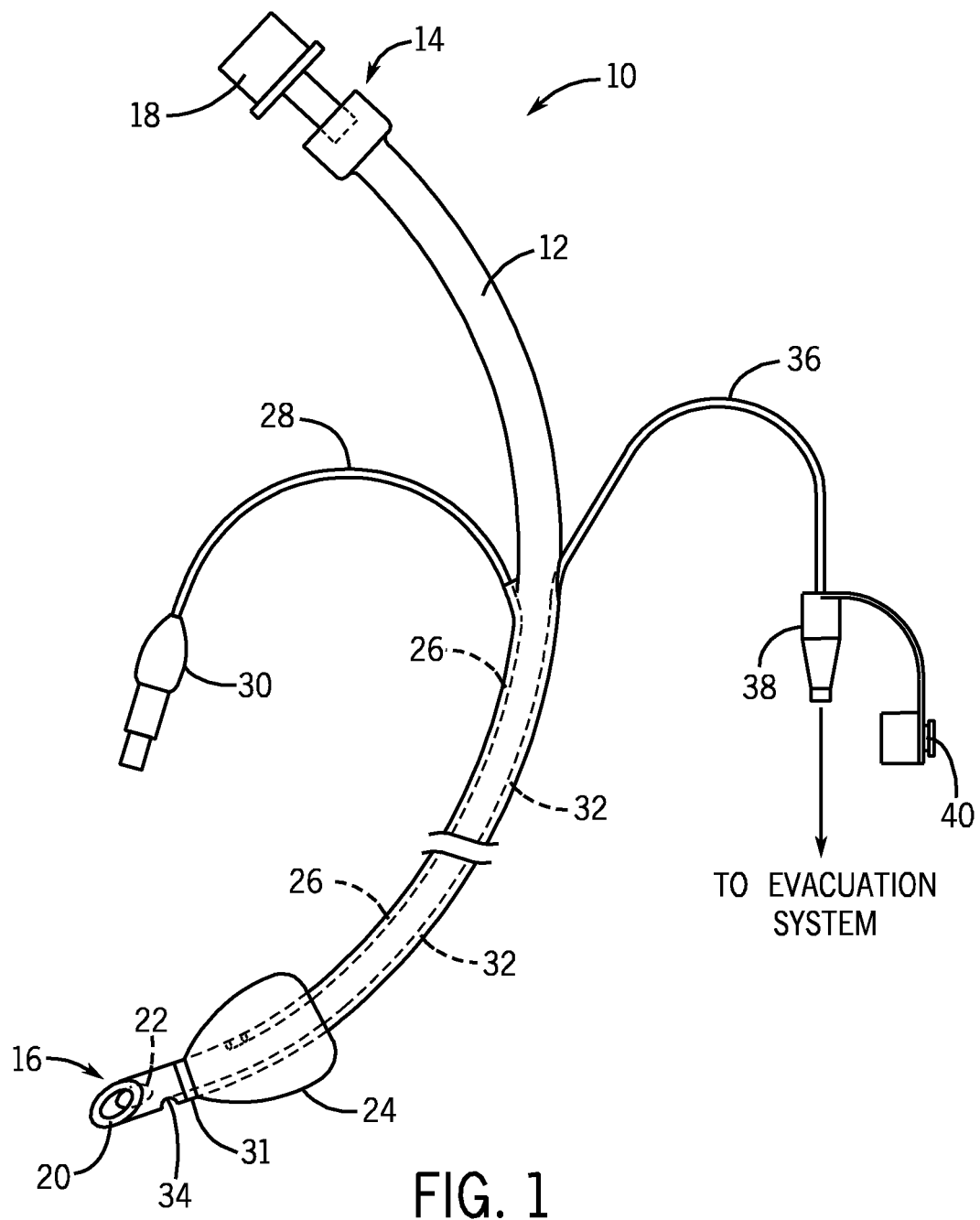
FIG. 1 is an elevational view of an exemplary endotracheal tube with a single port located below a cuff in accordance with aspects of the present disclosure.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed in further detail below, various embodiments of a tracheal tube are provided to suction accumulated mucus secretions from the airway of intubated patients. The tracheal tube is disposable rather than reusable, capable of suctioning below the cuff rather than exclusively above the cuff, capable of being used for drug delivery as well as fluid suctioning, capable of conveying gas to and from a patient, and so forth. The disclosed embodiments include a variety of endotracheal tubes with integral suction lumens terminating in ports optimally located at the distal end of the endrotracheal tubes between a Murphy's eye and a cuff. The ports are located sufficiently close to the cuff to disallow inadvertent contact between the suctioning ports and adjacent tissues when the cuff is inflated and the tracheal tube is placed such that it is centered within the trachea. Furthermore, the ports are located such that their openings face the posterior side of the patient during intubation in a conventional semirecumbent position. During intubation, the foregoing features, among others, of the tracheal tube and its associated ports may have the effect of preventing bacterial colonization of the respiratory airway and the subsequent development of ventilator associated pneumonia (VAP) in the lungs.

The devices and techniques provided herein may minimize the complexity of the system used to suction mucus from the patient's airway as compared to traditional designs because the suctioning system is integral with the main tubular body of the tracheal tube. That is, additional assemblies need not be attached to the tracheal tubes to enable suctioning capabilities; these capabilities are inherent in the design and manufacture of the tracheal tubes. In certain embodiments, the provided tracheal tubes and methods of operating the tracheal tubes may be used in conjunction with auxiliary devices, such as airway accessories, ventilators, humidifiers, and so forth, which may cooperate with the tracheal tubes to maintain airflow to the patient's lungs. For instance, auxiliary devices may be coupled to the tracheal tubes to enable timed suctioning of the mucus such that mucus flow though the suctioning lumen is established in the same direction and at the same time as airflow out of the patient during expiration.

Turning now to the drawings, FIG. 1 is an elevational view of an exemplary endotracheal tube 10 in accordance with aspects of the present disclosure. The endotracheal tube 10 includes a central tubular body 12 with proximal and distal ends 14 and 16, respectively. In the illustrated embodiment, the proximal end 14 is outfitted with a connector 18 that may be attached to a mechanical ventilator during operation. The distal end 16 terminates in an opening 20 and may be placed in a patient's trachea during operation to maintain airflow to and from the patient's lungs. A Murphy's eye 22 may be located on the tubular body 12 opposite the opening 20 to prevent airway occlusion when the tube assembly 10 is improperly placed within the patient's trachea.

As illustrated, a cuff 24 that may be inflated to seal against the walls of a body cavity (e.g., a trachea) may be attached to the distal end 16 of the tubular body 12. The cuff 24 may be inflated via an inflation lumen 26 terminating in an inflation tube 28 connected to a fixture 30 located at the proximal end 14 of the tubular body 12. A shoulder 31 of the cuff 24 secures the cuff 24 to the tubular body 12. In some embodiments, the shoulder 31 may be folded up inside a lower end of the cuff 24 (not shown). As illustrated, the tubular body 12 also includes a suction lumen 32 that extends from a location on the tracheal tube 10 positioned outside the body when in use to a location on the tubular body 16 below the cuff 24 and above the Murphy's eye 22. The suction lumen 32 terminates in a port 34 through which secretions may be aspirated. It should be noted that in further embodiments, a plurality of ports and dedicated suction lumens may be located radially around the tubular body 12 such that secretions may be aspirated from the airways of patients who may be periodically repositioned during long term intubation.

An exterior suction tube 36 connects to the suction lumen 32 for the removal of suctioned fluids. The suction tube 36 terminates outside the body during use in a fixture 38 with a cap 40 that allows the suction tube 36 to be connected to auxiliary equipment (e.g., vacuum, collection reservoir, and so forth) during suctioning and to be closed when not in use. During operation, the suction tube 36 may be connected to a vacuum that applies suction in a predetermined continuous or discontinuous manner such that mucus removal is synchronized with patient expiration. For instance, vacuum may be applied such that mucus flow through the suctioning lumen 32 is established in the same direction and at the same time as airflow out of the patient during expiration.

The tubular body 16 and the cuff 24 may be formed from materials having desirable mechanical properties (e.g., puncture resistance, pin hole resistance, tensile strength, and so forth) and desirable chemical properties (e.g., biocompatibility). In one embodiment, the walls of the cuff 24 may be made of a polyurethane (e.g., Dow Pellethane® 2363-80A) having suitable mechanical and chemical properties. In other embodiments, the walls of the cuff 24 may be made of a suitable polyvinyl chloride (PVC). In certain embodiments, the cuff 24 may be generally sized and shaped as a high volume, low pressure cuff that may be designed to be inflated to pressures between about 15 cm $H_2O$ and 30 cm $H_2O$.

During intubation, the endotracheal tube 10 is inserted into the trachea of a patient such that the port 34 is located towards the posterior side of the patient when the patient is resting in a typical semirecumbent position. After insertion, the cuff 24 may be inflated via a syringe connected to the inflation tube 28, thus holding the endotracheal tube 10 in position. During operation, when the cuff 24 is inflated and the endotracheal tube 10 is placed such that it is centered within the trachea, the port 34 is located sufficiently close to the cuff 24 to disallow inadvertent contact between the suctioning port 34 and the adjacent trachea. When the endotracheal tube 10 is placed in this manner, secretions accumulating under the cuff 24 may be removed via the port 34. Additionally, when desired, the port 34, the suctioning lumen 32, and the suctioning tube 36 may be used for the delivery of treatment modalities to the area below the cuff 24. The ability to suction secretions accumulated below the cuff 24 rather than exclusively above the cuff 24 offers distinct advantages over traditional systems. For instance, the port 34 below the cuff 24 allows targeting of the secretions that may be primarily responsible for the development of VAP with suctioning, treatment modalities, or a combination thereof.

A side view of the distal end 16 of the exemplary endotracheal tube 10 of FIG. 1 is shown in FIG. 2. As illustrated, the single port 34 is located below the shoulder 31 of the cuff 24 and above the Murphy's eye 22. It should be noted that the placement of the port 34 in this location optimizes the suctioning ability of the endotracheal tube 10. First, the single port 34 design offers advantages over devices with multiple ports along the length of a single suctioning lumen. For instance, applying a vacuum to the single suctioning lumen with multiple ports may result in a single port receiving all the suction (i.e., draw all of the air aspirated by the suction source), while other ports that may be in close proximity to accumulated mucus receive little or no suction (i.e., draw little or no air). Second, the location of the single port 34 in the illustrated embodiment offers additional advantages over designs with ports placed in different locations. For instance, in traditional designs, during operation, the curvature of the endotracheal tube 10 and the operator variability associated with placement in the patient may lead to an effective port location in close proximity to the tracheal wall. That is, in traditional designs, it is likely that suctioning may cause the port to contact the tracheal wall, possibly causing membrane damage, occlusion of the suction lumen, and the development of VAP due to bacterial colonization. Present embodiments, however, may avoid these deleterious effects via placement of the port 34 in close proximity to the cuff 24, which prevents contact between the port 34 and adjacent body cavities.

Figure 3:
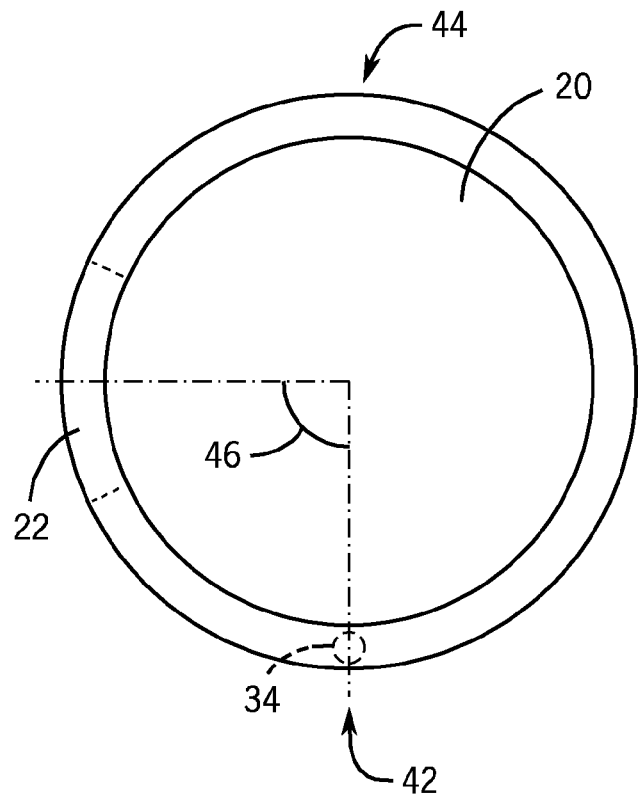
FIG. 3 is a bottom side view of the exemplary endotracheal tube of FIG. 1 in accordance with aspects of the present disclosure.

FIG. 3 further illustrates the placement of the port 34 in a bottom side view of the exemplary endotracheal tube 10 of FIG. 1. As illustrated, the port 34 is located such that when the endotracheal tube 10 is placed in the patient, the port 34 faces the posterior side of the patient, as represented by arrow 42. That is, when the endotracheal tube 10 is placed in the patient, the port 34 is directly opposite the anterior side of the patient, as represented by arrow 44. The port 34 is displaced from the center of the Murphy eye 22 by an angle 46. In the illustrated embodiment, the angle 46 is approximately 90 degrees. However, it should be noted that the particular angle 46 may be different. In the illustrated embodiment, the port 34 is located on the posterior side of the patient, as indicated by arrow 42, during operation. For instance, the port 34 may be radially located closer to or further from the Murphy's eye 22 such that the angle 46 is decreased or increased, respectively. Additionally, it should be noted that in other embodiments, the Murphy Eye 22 may be eliminated from the tubular body 12. In such embodiments, an edge of the port 34 may be located approximately 0 to 5 mm from an extremity of the shoulder 31. An advantageous radial position for the port 34 is still on the posterior side of the patient, as represented by arrow 42, when intubated.

Figure 4:
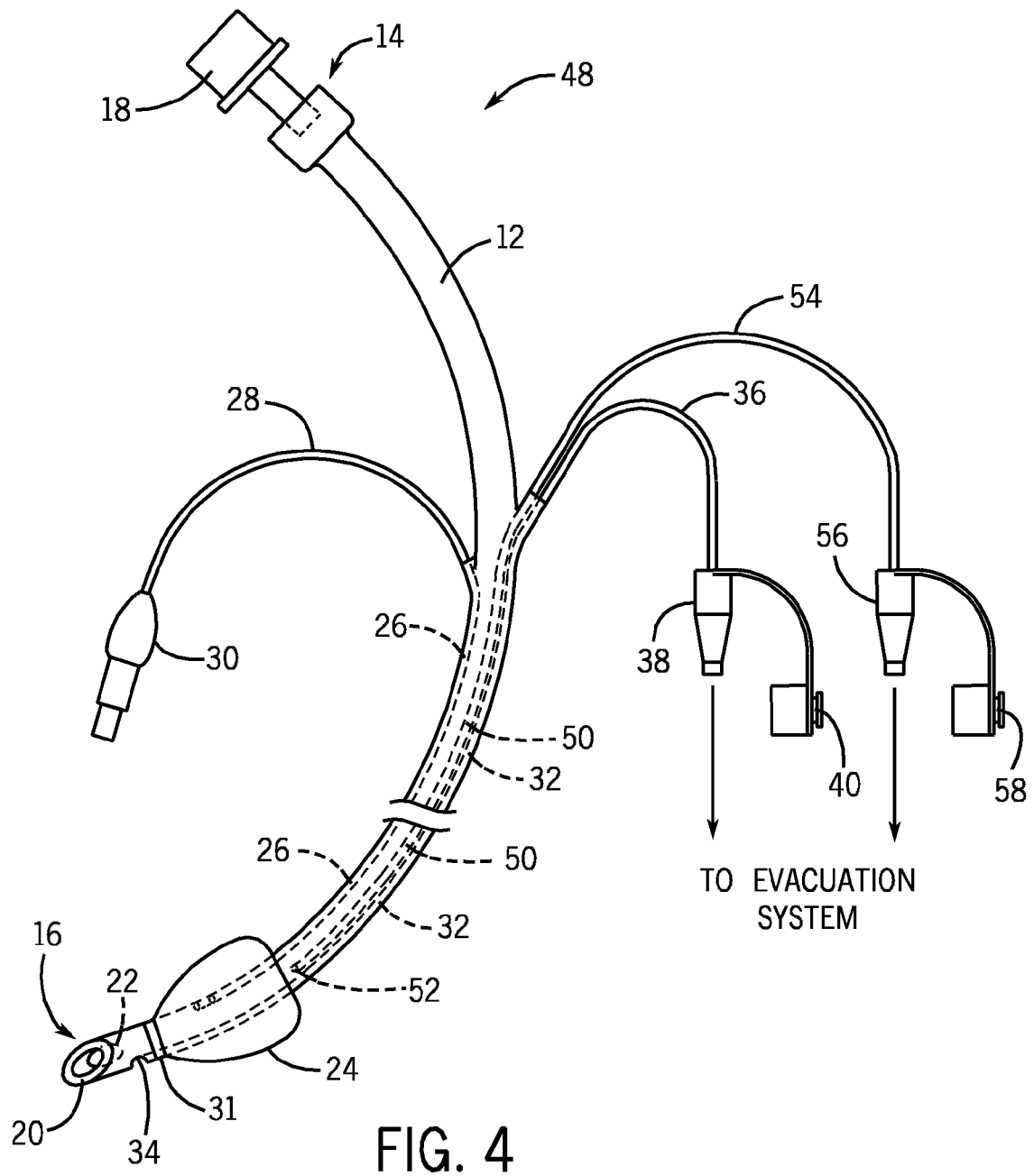
FIG. 4 is an elevational view of an exemplary endotracheal tube with a first port located above a cuff and a second port located below the cuff in accordance with aspects of the present disclosure.

FIG. 4 illustrates an exemplary endotracheal tube 48 in accordance with a further embodiment of the present disclosure. As previously described with respect to FIG. 1, the endotracheal tube 48 includes a central tubular body 12 with proximal and distal ends 14 and 16, respectively, wherein the proximal end 14 is outfitted with a connector 18 that may be attached to a mechanical ventilator during operation. The distal end 16 terminates in an opening 20 and may be placed in a patient's trachea during operation to maintain airflow to and from the patient's lungs. A Murphy's eye 22 may be located on the tubular body 12 opposite the opening 20 to prevent airway occlusion when the tube assembly 10 is improperly placed within the patient's trachea. The inflatable cuff 24 may be inflated via the inflation lumen 26 terminating in the inflation tube 28 connected to the fixture 30 located at the proximal end 18 of the tubular body 12. The shoulder 31 of the cuff 24 secures the cuff 24 to the tubular body 12. In some embodiments, the shoulder 31 may be folded up inside a lower end of the cuff 24 (not shown).

As in the embodiment of FIG. 1, the embodiment illustrated in FIG. 4 may include the suction lumen 32 that extends from a location on the tracheal tube 48 positioned outside the patient when in use to a location on the tubular body 16 below the cuff 24 and above the Murphy's eye 22. As before, the suction lumen 32 may terminate in a port 34 through which secretions located below the cuff 24 may be aspirated. It should be noted that in further embodiments, a plurality of ports and dedicated suction lumens may be located radially around the tubular body 12 such that secretions may be aspirated from the airways of patients who may be periodically repositioned during long term intubation. However, the embodiment of FIG. 4 also includes an additional suction lumen 50 that extends from near the proximal end 14 of the tubular body 12 positioned outside the patient when in use to a location adjacent to and above the cuff 24. The additional suction lumen 50 may terminate in an additional port 52 through which secretions located above the cuff 24 may be aspirated. Suction tubes 36 and 54 connect to suction lumens 32 and 50, respectively, for the removal of fluids suctioned through the ports 34 and 52. The suction tubes 36 and 54 terminate in fixtures 38 and 56 with caps 40 and 58 that allow the suction tubes 36 and 54 to be connected to auxiliary equipment (e.g., vacuum, collection reservoir, and so forth) during suctioning and to be closed when not in use.

The suction tubes 36 and 54 may be connected to a vacuum that applies suction in a predetermined continuous or discontinuous manner such that mucus removal is synchronized with patient expiration and/or coordinated between the two ports 34 and 52. For instance, as in previous embodiments, vacuum may be applied such that mucus flow through the suctioning lumens 32 and 50 is established in the same direction and at the same time as airflow out of the patient during expiration. Additionally, in this embodiment, vacuum may be applied such that alternating ports 34 or 52 are activated during each patient expiration cycle, both ports 34, 52 are activated during each respiration cycle, one or both ports 34 and/or 52 is manually selected by a caregiver during each respiration cycle, and so forth.

During intubation, the endotracheal tube 48 is inserted into the trachea of a patient such that the ports 34, 52 are located towards the posterior side of the patient when the patient is resting in the typical semirecumbent position. After insertion, the cuff 24 may be inflated via a syringe connected to the inflation tube 28, thus holding the endotracheal tube 48 in position. During operation, when the cuff 24 is inflated and the endotracheal tube 48 is placed such that it is centered within the trachea, the ports 34, 54 are located sufficiently close to the cuff 24 to disallow inadvertent contact between the suctioning ports 34, 54 and the adjacent trachea. When the endotracheal tube 10 is placed in this manner, secretions accumulating under the cuff 24 may be removed via the port 34, and secretions accumulating above the cuff 24 may be removed via the port 54. The port 34 located below the cuff, the suctioning lumen 32, and the suctioning tube 36 may be used for the delivery of treatment modalities to the area below the cuff 24 when desired. Similarly, the port 54 located above the cuff 24, the suctioning lumen 50, and the suctioning tube 54 may be used for the delivery of treatment modalities to the area above the cuff 24 when desired.

A side view of the distal end 16 of the exemplary endotracheal tube 48 of FIG. 4 is shown in FIG. 5. As illustrated, the port 34 below the cuff 24 is located below the shoulder 31 of the cuff 24 and above the Murphy's eye 22, whereas the port 52 above the cuff 24 is adjacent to the top of the cuff 24. It should be noted that the placement of the ports 34, 52 and the inclusion of a separate lumen 32 or 50 for each port 34 or 52 optimizes the suctioning ability of the endotracheal tube 48. As previously mentioned, traditional designs may apply a vacuum to a single suctioning lumen with multiple ports, possibly resulting in a single port receiving all the suction while other ports that may be in close proximity to accumulated mucus receive little or no suction. The present disclosure may overcome this disadvantage since each port 34 or 52 is exclusively connected to its designated suction lumen 32 or 50. Additionally, the location of the ports 34, 52 in the illustrated embodiment offers further advantages over traditional designs. In such designs, it is likely that suctioning may cause the ports to contact the tracheal wall, possibly causing membrane damage, occlusion of the suction lumen, and the development of VAP due to bacterial colonization. Present embodiments, however, may avoid these deleterious effects during operation via placement of the ports 34, 52 in close proximity to the cuff 24, which prevents contact between the port 34 and adjacent tissues when inflated.

Figure 6:
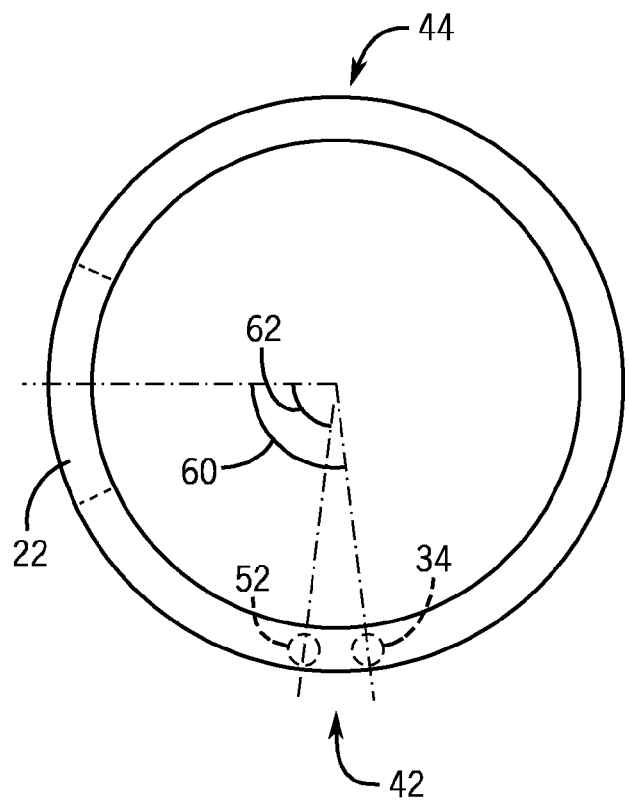
FIG. 6 is a bottom side view of the exemplary endotracheal tube of FIG. 4 in accordance with aspects of the present disclosure.

FIG. 6 further illustrates the placement of the ports 34, 52 in a bottom side view of the exemplary endotracheal tube 48 of FIG. 4. As illustrated, the ports 34, 52 are located such that when the endotracheal tube 48 is placed in the patient, the ports 34, 52 face the posterior side of the patient, as represented by arrow 42. That is, when the endotracheal tube 10 is placed in the patient, the ports 34, 52 are directly opposite the anterior side of the patient, as represented by arrow 44. The port 34 below the cuff 24 and the port 52 above the cuff 24 are displaced from the center of the Murphy's eye 22 by angles 60 and 62, respectively. In the illustrated embodiment, the angles 60, 62 are approximately 90 degrees. However, it should be noted that the angles 60, 62 may be any measure such that the ports 34, 52 are located on the posterior side of the patient, as indicated by arrow 42, during operation.

Figure 7:
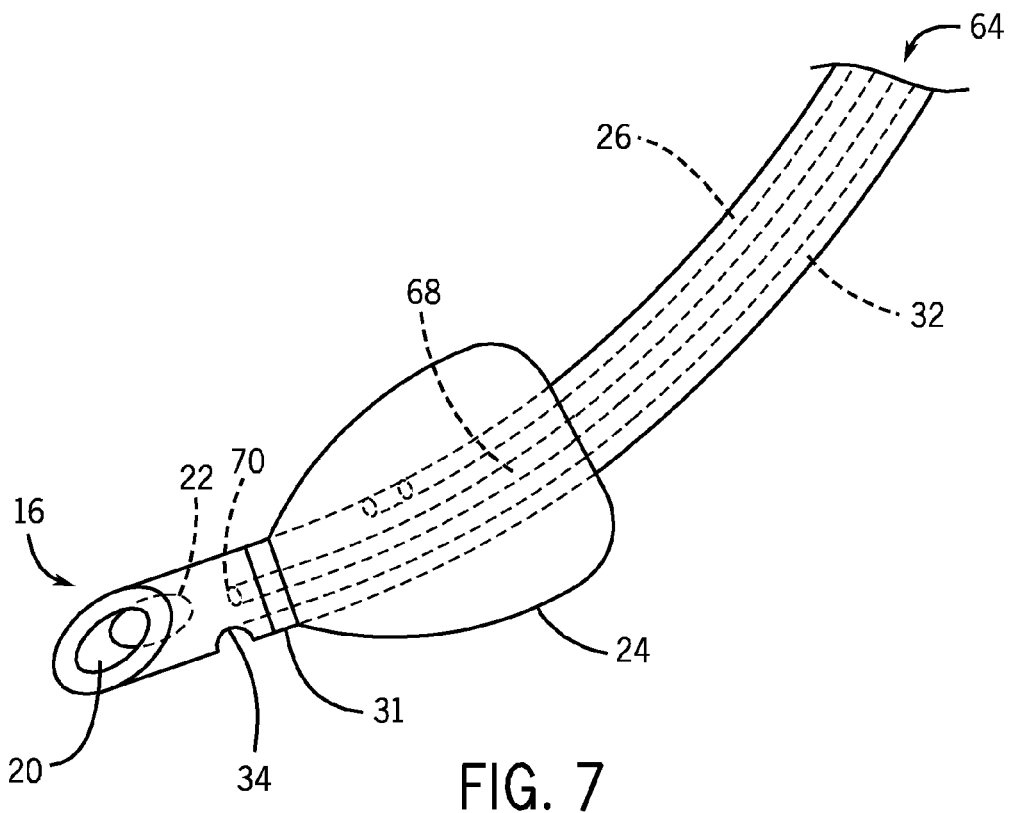
FIG. 7 is an elevational view of an exemplary endotracheal tube with two ports located below a cuff in accordance with aspects of the present disclosure.
Figure 8:
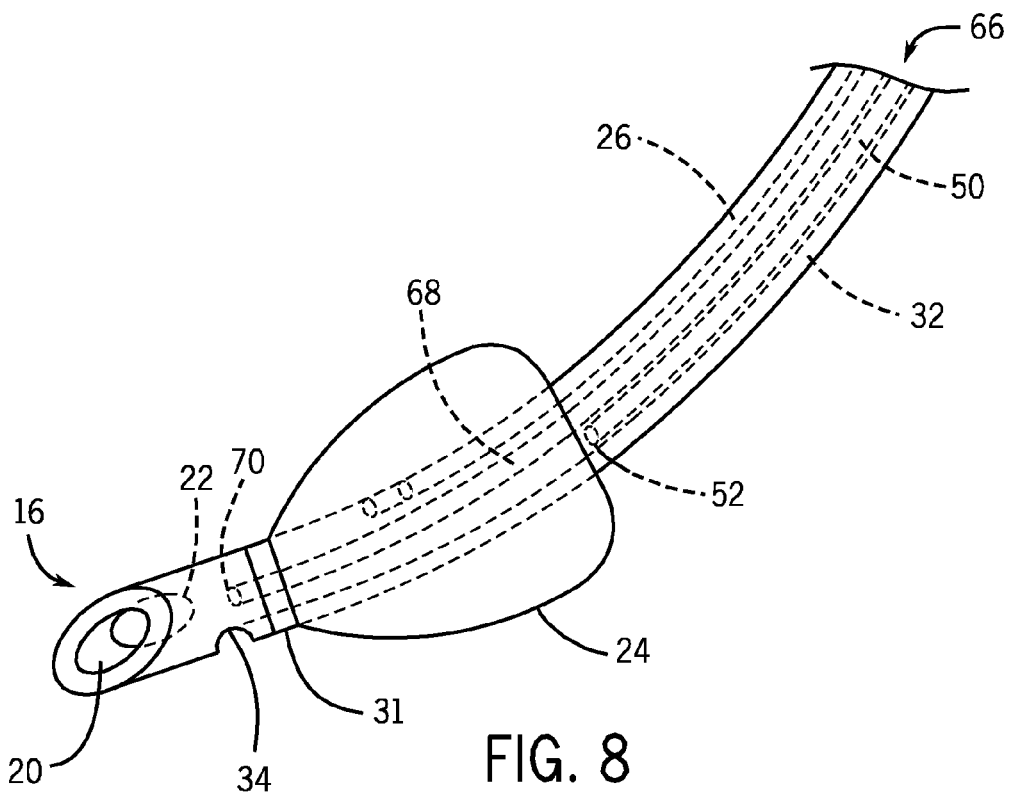

FIGS. 7 and 8 illustrate further embodiments of the endotracheal tubes 10, 48 disclosed in FIGS. 1 and 4, respectively. Exemplary endotracheal tubes 64, 66 are provided that include an additional lumen 68 that terminates below the cuff 24 in an additional port 70. The lumen 68 may be configured to cooperate with pressure sensors and/or pressure indicators that may be placed in locations along the lumen 66. During operation, the lumen 68 may extend to a location outside of the airway of the patient, possibly terminating in an inflation indicator that the operator may use to determine proper inflation of the cuff 24. In some embodiments, the lumen 68 may terminate in a pressure sensor that is configured to sense the pressure of the cuff 24.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A tracheal tube comprising:
   a tubular body comprising an open distal end for ventilating a patient, and a Murphy's eye adjacent to the open distal end;
   a cuff disposed around the tubular body above the Murphy's eye and configured to be inflated to seal the cuff against a wall of a patient trachea; and
   a suction lumen extending along the tubular body between a location on the tracheal tube positioned outside the patient when in use to a fixed location of a suction port on the tracheal tube below the cuff and above the Murphy's eye, and terminating in the port through which secretions may be aspirated via the suction lumen.

2. The tracheal tube of claim 1, comprising a shoulder below the cuff configured to secure the cuff to the tubular body, and wherein an edge of the port is disposed approximately 0 to 5 mm from a lower extremity of the shoulder.

3. The tracheal tube of claim 1, wherein the port is disposed on a side of the tubular body that is oriented posteriorly following intubation of the patient.

4. The tracheal tube of claim 1, comprising at least one additional lumen extending along the tubular body and terminating below the cuff, and wherein the lumen is configured to be a dedicated passageway for evacuation of secretions collecting on an outer surface of the tubular body below the cuff.

5. The tracheal tube of claim 1, wherein the suction lumen is configured to allow the conveyance of treatment modalities.

6. A tracheal tube comprising:
   a tubular body comprising an open distal end for ventilating a patient and a Murphy's eye adjacent to the open distal end;
   a cuff disposed around the tubular body above the Murphy's eye and configured to be inflated to seal the cuff against a wall of a patient's trachea;
   a first suction lumen extending along the tubular body from near a proximal end of the tracheal tube positioned outside the patient when in use to a fixed location of a first suction port opening below the cuff and above the Murphy's eye, and terminating in the first port opening from a side of the tubular body through which secretions may be aspirated via the first suction lumen; and
   a second suction lumen extending along the tubular body from near the proximal end of the tracheal tube positioned outside the patient when in use to a fixed location above the cuff, and terminating in a second port opening from the side of the tubular body through which secretions may be aspirated via the second suction lumen.

7. The tracheal tube of claim 6, wherein the first suction lumen and the first port are disposed on a side of the tubular body that is oriented posteriorly following intubation of the patient.

8. The tracheal tube of claim 7, wherein the second suction lumen and the second port are disposed on a side of the tubular body that is oriented posteriorly following intubation of the patient.

9. The tracheal tube of claim 7, wherein the first and second ports are radially displaced with respect to the Murphy's eye by approximately 90 degrees.

10. The tracheal tube of claim 6, comprising a shoulder below the cuff, configured to secure the cuff to the tubular body, and wherein an edge of the first port is disposed approximately 0 to 5 mm from a lower extremity of the shoulder.

11. The tracheal tube of claim 6, wherein the first port and the second port are disposed on a side of the tubular body that is oriented posteriorly following intubation of the patient.

12. The tracheal tube of claim 6, comprising at least one additional lumen extending along the tubular body and terminating below the cuff, and wherein the lumen is configured to be a dedicated passageway for evacuation of secretions collecting on an outer surface of the tubular body below the cuff.

13. The tracheal tube of claim 6, wherein the first suction lumen, the second suction lumen, or a combination thereof are configured to allow the conveyance of treatment modalities.

14. A method of operation for a tracheal tube comprising:
   providing a tracheal tube, wherein the tracheal tube comprises a tubular body comprising a Murphy's eye adjacent to an open distal end for ventilating a patient, a cuff disposed around the tubular body above the Murphy's eye, and a suction lumen extending along the tubular body between a location on the tracheal tube positioned outside the patient when in use and a fixed location of a suction port on the tracheal tube below the cuff and above the Murphy's eye and terminating in the suction port through which secretions may be aspirated via the suction lumen;
   intubating a patient with the tracheal tube;
   inflating the cuff against the trachea of the patient;
   ventilating the patient; and
   removing fluids from an area below the cuff via the suction lumen and the suction port.

15. The method of claim 14, wherein removing fluids comprises suctioning at predetermined time points.

16. The method of claim 14, wherein providing a tracheal tube comprises providing a second suction lumen extending along the tubular body from near a proximal end of the tracheal tube positioned outside the patient when in use to a location above the cuff terminating in a second port opening from the side of the tubular body.

17. The method of claim 16, comprising removing fluids from an area above the cuff via the second suction lumen and the second port.

18. A tracheal tube comprising:
   a tubular body comprising an open distal end for ventilating a patient, and a Murphy's eye adjacent to the open distal end;
   a cuff disposed around the tubular body above the Murphy's eye and the open distal end and configured to be inflated to seal the cuff against a wall of a trachea of a patient; and
   a suction lumen extending along the tubular body between a location on the tracheal tube positioned outside the patient when in use to a fixed location of a suction port on the tracheal tube below the cuff and above the Murphy's eye, and terminating in the port through which secretions may be aspirated via the suction lumen.

19. The tracheal tube of claim 18, comprising a shoulder below the cuff configured to secure the cuff to the tubular body, and wherein an edge of the port is disposed approximately 0 to 5 mm from a lower extremity of the shoulder.

20. The tracheal tube of claim 18, wherein the port is disposed on a side of the tubular body that is oriented posteriorly following intubation of the patient.

* * * * *